US009844529B2

(12) United States Patent
Chan et al.

(10) Patent No.: US 9,844,529 B2
(45) Date of Patent: Dec. 19, 2017

(54) COMBINATION THERAPY FOR OVARIAN CANCER

(71) Applicant: Eli Lilly And Company, Indianapolis, IN (US)

(72) Inventors: Edward Michael Chan, Greenwood, IN (US); Susan Elizabeth Pratt, Zionsville, IN (US); Louis Frank Stancato, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/354,244

(22) PCT Filed: Oct. 31, 2012

(86) PCT No.: PCT/US2012/062634
§ 371 (c)(1),
(2) Date: Apr. 25, 2014

(87) PCT Pub. No.: WO2013/070460
PCT Pub. Date: May 16, 2013

(65) Prior Publication Data
US 2014/0302174 A1 Oct. 9, 2014

Related U.S. Application Data

(60) Provisional application No. 61/558,582, filed on Nov. 11, 2011.

(51) Int. Cl.
*A61K 31/437* (2006.01)
*A61K 31/555* (2006.01)
*A61K 31/282* (2006.01)
*A61K 31/24* (2006.01)
*A61K 31/7068* (2006.01)
*A61K 33/24* (2006.01)

(52) U.S. Cl.
CPC .......... *A61K 31/282* (2013.01); *A61K 31/437* (2013.01); *A61K 31/555* (2013.01); *A61K 31/7068* (2013.01); *A61K 33/24* (2013.01)

(58) Field of Classification Search
None
See application file for complete search history.

(56) References Cited

FOREIGN PATENT DOCUMENTS

WO   00/38519       7/2000
WO   2005/075478 A1 8/2005

OTHER PUBLICATIONS

Belpommea et al. (Gynecologic Oncology, 91(1):32-38, 2003).*
PDF copy regarding FDA approval of Gemzar/Carboplatin from Cancer Network (p. 1, 2006).*
Mader et al: "Imidazolyl benzimidazoles and imidazo[4,5-b]pyridines as potent p38alpha MAP kinase inhibitors with excellent in vivo antiinflanmatory properties", Bioorganic & Medicinal Chemistry Letters. Pergamon. Elsevier Science, GB, vol. 18, No. 1, Nov. 1, 2007, pp. 179-183, XP022410879, ISSN: 0960-894X, DOI: 10.1016/J.BMCL.2007.10.106 compound 40.
Matrone Antonio et al: "p38alpha is required for ovarian cancer cell metabolism and survival.", International Journal of Gynecological, Cancer : Official Journal of the International Gynecological Cancer Society Feb 2010, vol. 20, No. 2, Feb. 2010, pp. 203-211, XP009165129, ISSN: 1525-1438, the whole document.
Jiao Jin-Wen et al: "Tanshinone IIA acts via p38 Mark to induce apoptosis and the down-regulation of ERCCI and lung-resistance protein in cisplatin-resistant ovarian cancer cells.", Oncology Reports Mar. 2011, vol. 25, No. 3, Mar. 2011. pp.781-788, XPOO9165120, ISSN: 1791-2431, the whole document.
Internal Experimental Protocol and Results Authored by Named Inventor on U.S. Appl. No. 14/354,244, Susan Elizabeth Pratt.
Japanese Office Action dated Jul. 12, 2016.
Menon_SB202190-Induced Cell type-Specific Vacuole Formation and Defective Autophagy Do Not Depend on p35 MAP Kinase Inhibition_HUMPLoS ONE_V. 6_.i 8_2011.
Humphrey_The 2016 WHO Classification of Tumours of the Urinary System and Male Genital Organs—Part B: Prostate and Bladder Tumours_European Urology_V.70_pp. 106-119_2016.
Patnaik, et al, "A First-in-Human Phase I Study of the Oral p38 MAPK Inhibitor, Ralimetinib (LY2228820 Dimesylate), In Patients with Advanced Cancer", Clinical Cancer Research, p. 1095-1102, vol. 22, issue 5, (Mar. 2016).
"Sustained activation of JNK/p38 MAPK pathways in response to cisplatin leads to Fas ligand induction and cell death in ovarian carcinoma cells." Mansouri A, Ridgway LD, Korapati AL, Zhang Q, Tian L, Wang Y, Siddik ZH, Mills GB, Claret FX. J Biol Chem. May 23, 2003;278(21):19245-56.
"p38 MAPK turns hepatocyte growth factor to a death signal that commits ovarian cancer cells to chemotherapy-induced apoptosis." Coltella N, Rasola A, Nano E, Bardella C, Fassetta M, Filigheddu N, Graziani A, Comoglio PM, Di Renzo MF. Int J Cancer. Jun. 15, 2006;118(12):2981-90.
Antitumor properties of salinomycin on cisplatin-resistant human ovarian cancer cells in vitro and in vivo: involvement of p38 MAPK activation. Zhang B, Wang X, Cai F, Chen W, Loesch U, Zhong XY. Oncol Rep. Apr. 2013;29(4):1371-8.
Epigallocatechin 3 gallate inhibits the proliferation and migration of human ovarian carcinoma cells by modulating p38 kinase and matrix metalloproteinase 2. Wang F, Chang Z, Fan Q, Wang L. Mol Med Rep. Mar. 2014;9(3):1085-9.
CHM-1 induces apoptosis via p38-mediated upregulation of DR5 expression in human ovarian cancer SKOV3 cells.Lee JC, Chou LC, Huang CH, Chung JG, Huang LJ, Lee KH, Hung MC, Way TD, Kuo SC. Eur J Pharmacol. Nov. 16, 2011;670(1):96-104.
Tubeimoside I sensitizes cisplatin in cisplatin-resistant human ovarian cancer cells (A2780/DDP) through down-regulation of ERK and up-regulation of p38 signaling pathways. Liu HZ, Yu C, Yang Z, He JL, Chen WJ, Yin J, Li WM, Liu HT, Wang YX. Mol Med Rep. Sep.-Oct. 2011;4(5):985-92.

(Continued)

*Primary Examiner* — Bong-Sook Baek
(74) *Attorney, Agent, or Firm* — Tina M. Tucker

(57) ABSTRACT

The present invention provides a method of treating ovarian cancer in a mammal in need of such treatment comprising administering an effective amount of a combination of gemcitabine, cisplatin or carboplatin, and 5-[2-tert-butyl-5-(4-fluoro-phenyl)-1H-imidazol-4-yl]-3-(2,2-dimethyl-propyl)-3H-imidazo[4,5-b]pyridin-2-ylamine.

10 Claims, No Drawings

(56) References Cited

OTHER PUBLICATIONS

Curcumin-induced apoptosis in ovarian carcinoma cells is p53-independent and involves p38 mitogen-activated protein kinase activation and downregulation of Bcl-2 and survivin expression and Akt signaling. Watson JL, Greenshields A, Hill R, Hilchie A, Lee PW, Giacomantonio CA, Hoskin DW. Mol Carcinog. Jan. 2010;49(1):13-24.

ESMO Clinical Practice Guidelines—Gynecological Cancers (2013).

Centers for Disease Control—What is Gynecologic Cancer (2014).

* cited by examiner

COMBINATION THERAPY FOR OVARIAN CANCER

Ovarian cancer is the second most common gynecologic cancer and the deadliest in terms of absolute number. Treatment usually involves chemotherapy and surgery, and sometimes radiotherapy.

Unfortunately, a cure for ovarian cancer still remains elusive and there exists a need for more and different therapies that may prove to be effective in treating ovarian cancer.

Several classes of anti-cancer drugs used to treat various types of cancers including ovarian cancer have been identified, including platinum containing drugs and pyrimidine analogs. Cisplatin (also known as cisplatinum or cis-diamminedichloroplatinum(II)) was the first member of a class of platinum-containing anti-cancer drugs, which now also includes carboplatin. These platinum complexes react in vivo, binding to and causing crosslinking of DNA, which ultimately triggers apoptosis (programmed cell death).

Gemcitabine hydrochloride (hereafter referred to as gemcitabine) is a pyrimidine analog. It is currently used to treat various types of cancers including in combination with carboplatin for the treatment of ovarian cancer.

While it is reported in the literature that gemcitabine plus cisplatin is a well tolerated and active regimen in patients with recurrent ovarian cancer, the present inventors have discovered that when these agents are used in combination with 5-[2-tert-butyl-5-(4-fluoro-phenyl)-1H-imidazol-4-yl]-3-(2,2-dimethyl-propyl)-3H-imidazo[4,5-b]pyridin-2-ylamine, a compound disclosed in U.S. Pat. No. 7,582,652 that is currently undergoing clinical investigation as a possible treatment for a variety of cancer indications, the triple combination provides an improvement in efficacy over the combination of gemcitabine plus cisplatin.

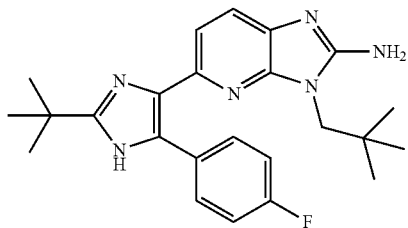 [SMILES: CC(C)(C)Cn1c(N)nc2ccc(-c3nc(C(C)(C)C)[nH]c3-c3ccc(F)cc3)nc21]

5-[2-tert-butyl-5-(4-fluoro-phenyl)-1H-imidazol-4-yl]-3-(2,2-dimethyl-propyl)-3H-imidazo[4,5-b]pyridin-2-ylamine Furthermore, since the combination of carboplatin and gemcitabine are also currently used for the treatment of ovarian cancer, and it is also reported in the literature that comparable efficacy is seen in the treatment of ovarian cancer between carboplatin compared to cisplatin (however with less toxicity observed with carboplatin), the current inventors conclude that the triple combination of gemcitabine, carboplatin, and 5-[2-tert-butyl-5-(4-fluoro-phenyl)-1H-imidazol-4-yl]-3-(2,2-dimethyl-propyl)-3H- imidazo[4,5-b]pyridin-2-ylamine may be more efficacious than a combination of gemcitabine and carboplatin along with the potential benefit of reduced toxicity by administering carboplatin instead of cisplatin.

The present invention relates to a method of treating ovarian cancer in a mammal comprising administering a combination of gemcitabine, a platinum agent selected from the group consisting of cisplatin and carboplatin, and 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt. In a further embodiment, administration is on the same day. In another further embodiment, the administration is during a 21-day treatment cycle. In another further embodiment, gemcitabine and the platinum agent are administered up to 2 days after 5-[2-tert-butyl-5-(4-fluoro-phenyl)-1H-imidazol-4-yl]-3-(2,2-dimethyl-propyl)-3H-imidazo[4,5-b]pyridin-2- ylamine or a pharmaceutically acceptable salt is administered and gemcitabine is administered again up to 7 days later. In another further embodiment, the pharmaceutically acceptable salt is the dimethanesulfonate salt.

The present invention also relates to a method of treating ovarian cancer in a mammal undergoing concurrent therapy with 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt thereof comprising administering a combination of gemcitabine and a platinum agent selected from the group consisting of cisplatin and carboplatin. In a further embodiment, the pharmaceutically acceptable salt is the dimethanesulfonate salt.

The present invention also relates to a method of treating ovarian cancer in a mammal undergoing concurrent therapy with 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt thereof and a platinum agent selected from the group consisting of cisplatin and carboplatin comprising administering gemcitabine. In a further embodiment, the pharmaceutically acceptable salt is the dimethanesulfonate salt.

The present invention also relates to a method of treating ovarian cancer in a mammal undergoing concurrent therapy with 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt thereof and gemcitabine comprising administering a platinum agent selected from the group consisting of cisplatin and carboplatin. In a further embodiment, the pharmaceutically acceptable salt is the dimethanesulfonate salt.

The present invention also relates to a method of treating ovarian cancer in a mammal undergoing concurrent therapy with gemcitabine and a platinum agent selected from the group consisting of cisplatin and carboplatin comprising administering 5-[2-tert-butyl-5-(4-fluoro-phenyl)-1H-imidazol-4-yl]-3-(2,2-dimethyl-propyl)-3H- imidazo[4,5-b]pyridin-2-ylamine or a pharmaceutically acceptable salt thereof. In a further embodiment, the pharmaceutically acceptable salt is the dimethanesulfonate salt.

The present invention also relates to 5-[2-tert-butyl-5-(4-fluoro-phenyl)-1H-imidazol-4-yl]-3-(2,2-dimethyl-propyl)-3H-imidazo[4,5-b]pyridin-2- ylamine, or a pharmaceutically acceptable salt thereof, for use in combination therapy with gemcitabine and a platinum agent selected from cisplatin and carboplatin in the treatment of ovarian cancer. In a further embodiment, the administration of 5-[2-tert-butyl-5-(4-fluoro-phenyl)-1H-imidazol-4-yl]-3-(2,2-dimethyl-propyl)-3H-imidazo[4,5-b]pyridin-2-ylamine, or a pharmaceutically acceptable salt thereof, precedes that of gemcitabine and the platinum agent. In another further embodiment, the administration of 5-[2-tert-butyl-5-(4-fluoro-phenyl)-1H-imidazol-4-yl]-3-(2,2-dimethyl-propyl)-3H-imidazo[4,5-b]pyridin-2-ylamine, or a pharmaceutically acceptable salt thereof, gemcitabine and the platinum agent is within 24 hours. In another further embodiment, gemcitabine and the platinum agent are administered up to 2 days after administration of 5-[2-tert-butyl-5-(4-fluoro-phenyl)-1H-imidazol-4-yl]-3-(2,2-dimethyl-propyl)-3H-imidazo[4,5-b]pyridin-2-ylamine, or a pharmaceutically acceptable salt thereof, and gemcitabine is administered again up to 7 days later. In another further embodiment, administration of gemcitabine and the platinum agent precedes that of 5-[2-tert-butyl-5-(4-fluoro-phenyl)-1H-imidazol-4-yl]-3-(2,2-dimethyl-propyl)-3H-imidazo[4,5-b]pyridin-2-ylamine, or a pharmaceutically acceptable salt thereof. In another further embodiment, gemcitabine and the platinum agent are administered simultaneously. In another further embodiment, the platinum agent is cisplatin. In another further embodiment, the platinum agent is carboplatin. In another further embodiment, the administration is during a 21-day treatment cycle. In another further embodiment, the pharmaceutically acceptable salt is the dimethanesulfonate salt.

The present invention also relates to the use of 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt in the manufacture of a medicament for the treatment of ovarian cancer wherein said medicament is to be administered in combination with a platinum agent and gemcitabine. In a further embodiment, the administration of 5-[2-tert-butyl-5-(4-fluoro-phenyl)-1H-imidazol-4-yl]-3-(2,2-dimethyl-propyl)-3H- imidazo[4,5-b]pyridin-2-ylamine or a pharmaceutically acceptable salt precedes that of gemcitabine and the platinum agent. In another further embodiment, the administration of 5-[2-tert-butyl-5-(4-fluoro-phenyl)-1H-imidazol-4-yl]-3-(2,2-dimethyl-propyl)-3H- imidazo[4,5-b]pyridin-2-ylamine or a pharmaceutically acceptable salt, gemcitabine, and the platinum agent is within 24 hours. In another further embodiment, gemcitabine and the platinum agent are administered up to 2 days after 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt is administered and gemcitabine is administered again up to 7 days later. In another further embodiment, administration of gemcitabine and the platinum agent precedes that of 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt thereof. In another further embodiment, gemcitabine and the platinum agent are administered simultaneously. In another further embodiment the platinum agent is cisplatin. In another further embodiment the platinum agent is carboplatin. In another further embodiment thereof, the administration is during a 21-day treatment cycle. In another further embodiment, the pharmaceutically acceptable salt is the dimethanesulfonate salt.

5-[2-Tert-butyl-5-(4-fluoro-phenyl)-1H-imidazol-4-yl]-3-(2,2-dimethyl-propyl)-3H-imidazo[4,5-b]pyridin-2-ylamine can be made according to the procedures as described in U.S. Pat. No. 7,582,652. Alternatively, the molecule can be made following procedures provided herein. The reagents and starting materials are readily available to one of ordinary skill in the art or may be made by procedures which are selected from standard techniques of organic and heterocyclic chemistry, or techniques which are analogous to the syntheses of known structurally similar compounds. The naming of the following Preparations and Reference Example 1 is generally done using the IUPAC naming feature in Symyx Isentris® version 3.2.

Preparation 1

6-Chloro-N-(2,2-dimethylpropyl)-3-nitro-pyridin-2-amine

2,6-Dichloro-3-nitropyridine (30 g, 152.34 mmol) is dissolved in methyl tert-butyl ether (300 mL) to obtain a yellow solution which is then cooled to 0-5° C. To this solution is added triethylamine (20 mL, 143.49 mmol), followed by a slow addition of neopentylamine (16 mL, 136.40 mmol). After the addition is complete the reaction mixture is stirred at 5° C. for 2 hours and then at room temperature overnight. The next day (after about 18 hours) the reaction is shown as complete by thin layer chromatography (20% ethyl acetate in hexane). The reaction mixture is washed with water (100 mL) and brine (100 mL). The organic portion is dried over MgSO$_4$, filtered, and then concentrated to a residue. Isopropyl alcohol (20 mL) is added. Crystals appear and are collected by filtration with washing using cold isopropyl alcohol (15 mL) to obtain the title compound (32 g, 86%).

Preparation 2

5-Chloro-3-(2,2-dimethylpropyl)imidazo[4,5-b]pyridin-2-amine hydrobromide

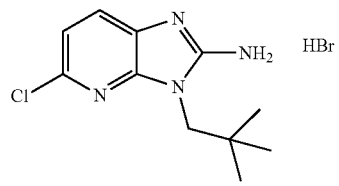 [SMILES: CC(C)(C)Cn1c(N)nc2ccc(Cl)nc21 ; Br]

6-Chloro-N-(2,2-dimethylpropyl)-3-nitro-pyridine-2-amine (24.4 g, 0.10 mol) is charged into a 1 L autoclave with toluene (300 mL).

In a beaker 5% Pt/C (1.5 g) is mixed with water (12 mL) and 50% hypophosphorous acid (0.25 mL) with stirring for 10 minutes. The Pt/C catalyst preparation is charged into the autoclave. The reaction mixture is heated to 75° C. at 50 psi of hydrogen. After 3 hours, GC analysis indicates the starting material is less than 1% present. The reaction is stopped and cooled down to room temperature. The reaction mixture is filtered through a pad of CELITE® and the filter cake rinsed with methanol. The filtrate containing the product, 6-chloro-N2-(2,2-dimethylpropyl)pyridine-2,3-diamine, is concentrated under vacuum to a volume of about 100 mL and used directly in the cyclization without further purification.

The above solution is diluted with methanol (150 mL) and cooled in an ice bath. Cyanogen bromide (11 g, 0.105 mol) is added in one portion. The reaction is allowed to warm to ambient temperature with stirring as the ice bath warms up.

The reaction is complete after about 5 to 10 hours.

The reaction mixture is concentrated under vacuum to about 4 volumes (to collect about 6 volumes of distillate) under vacuum. Methyl tert-butyl ether (6 volumes, 180 mL) is added. The mixture is cooled in an ice bath and stirred for 1 hour. The material is filtered to provide the title compound (22.0 g, 76%) as an off-white solid.

Preparation 3

3-(2,2-Dimethylpropyl)-5-[(E)-2-(4-fluorophenyl)vinyl]imidazo[4,5-b]pyridin-2-amine

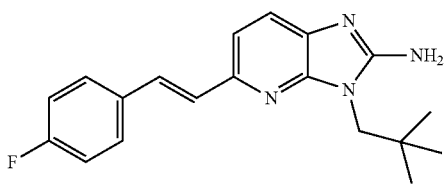 [SMILES: CC(C)(C)Cn1c(N)nc2ccc(/C=C/c3ccc(F)cc3)nc21]

Bis(di-tert-butyl(4-dimethylaminophenyl)phosphine)dichloropalladium(II) (CAS No: 887919-35-9) (100.4 mg, 141.8 μmol) is charged to a pear shaped flask and the solid deoxygenated with 5 vacuum/nitrogen cycles. 1-Butanol (55 mL) is added and then the flask contents are deoxygenated with 3 vacuum (30 sec each)/nitrogen cycles followed by 2 more vacuum (60 sec each)/nitrogen cycles with stirring. A complete solution is not achieved, but rather a hazy mixture.

To a 3-neck, round-bottomed flask equipped with a Claisen adapter, mechanical stirrer, thermocouple, reflux condenser, and rubber septum is added 5-chloro-3-(2,2-dimethylpropyl)imidazo[4,5-b]pyridin-2-amine hydrobromide (22.65 g, 70.9 mmol), and then the headspace is deoxygenated with a slight nitrogen sweep for 15 minutes. To the fluffy white solid is added 1-butanol (46 mL), diisopropylethylamine (34.48 g, 46.5 mL, 266.8 mmol), and 4-fluorostyrene (11.66 g; 11.4 mL, 95.5 mmol), each via syringe. After deoxygenating this mixture by sparging with nitrogen for 40 minutes, the catalyst/butanol mixture is added via syringe. The slurry is sparged for 10 minutes with nitrogen, and then the headspace is swept for 5 minutes with nitrogen. The reaction is allowed to stir at 118-120° C. overnight. After 18 hours, the mixture is cooled with stirring. Precipitation or crystallization occurs between 45° C. and 70° C. Starting at a temperature of 41° C., deionized water (100 mL) is added dropwise over 10 minutes to yield a slurry. After stirring and cooling to 26° C., an ice bath is applied for cooling the flask contents. After 1 hour, ethanol and more ice are added to the bath and the temperature is lowered to −2° C. The mixture is held at −2 to −5° C. for 1 hour, then filtered through a polypropylene pad (good filtration), rinsed with deionized water (4 volumes), followed by heptane (3 volumes). The material is pulled air dry by vacuum for 10 minutes and further dried in a vacuum oven at 40° C. to provide the title compound as an off-white solid (20.25 g, 88%).

$^1$H NMR (300 MHz, DMSO-$d_6$): δ 7.51 (m, 2H); 7.41 (d, 1H); 7.32 (d, 1H); 7.19 (m, 3H); 7.08 (d, 1H); 6.79 (s, 2H); 3.89 (s, 2H); 1.00 (s, 9H).

Preparation 4

1-[2-Amino-3-(2,2-dimethylpropyl)imidazo[4,5-b]pyridin-5-yl]-2-4-fluorophenyl)ethane-1,2-dione

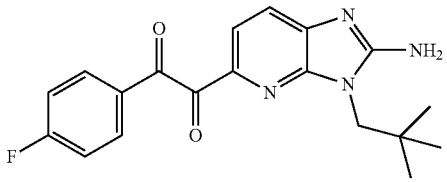 [SMILES: CC(C)(C)Cn1c(N)nc2ccc(C(=O)C(=O)c3ccc(F)cc3)nc21]

3-(2,2-Dimethylpropyl)-5-[(E)-2-(4-fluorophenyl)vinyl]imidazo[4,5-b]pyridine-2-amine (100.0 g, 308.26 mmol) is mixed with dimethyl sulfoxide (200 mL) in a 2 L, 3-neck, round-bottomed flask equipped with a reflux condenser, thermocouple, and mechanical stirrer. After stirring for 10 minutes, 48% hydrogen bromide (28.69 g, 170.20 mmol) is added over 4 minutes to the gray slurry. An exotherm from 22° C. to 33° C. is observed. To the reaction mixture is added acetic acid (9.28 g, 154.53 mmol). After stirring 1.8 hours, additional 48% hydrogen bromide (31.75 g, 188.35 mmol) is added. The reaction mixture is heated and becomes thick. Acetic acid (400 mL, 6.98 mol) is added. After reaching 91° C., dimethyl sulfoxide (50 mL) and 40% $H_2SO_4$ (100 mL) are added. The temperature is increased to 100° C. After 3 hours, additional 40% $H_2SO_4$ (300 mL) is added and a Dean-Stark trap is installed to remove low boiling solvents such as dimethyl sulfide. After stirring another 17 hours at 100° C., another portion of 40% $H_2SO_4$ (80 mL) is charged to the reaction. The reaction is stirred 1 hour and then deionized water (300 mL) is added. The reaction is stirred for 3 hours and then the temperature is increased to 103° C. followed by addition of more deionized water (200 mL). After 2.5 hours more of stirring another portion of deionized water (200 mL) is added. Stirring and heating is continued another 1.5 hours at which time the heat is shut off (28 hours total from the time of the first addition of 40% $H_2SO_4$). The reaction mixture is allowed to crystallize, while cooling to ambient temperature overnight. The product is filtered, rinsed with deionized water (2×200 mL), and then dried in a vacuum oven at 50° C.

The solid material (as the salt) is treated with 1 M sodium hydroxide (550 mL) with stirring for 18 hours. The slurry is filtered, rinsed with deionized water (500 mL), and dried in a vacuum oven at 50° C. to afford the title compound (83.7 g, 77%). $^1$H NMR (300 MHz, DMSO-$d_6$): δ 7.95 (d, 1H); 7.87 (m, 2H); 7.60 (d, 1H); 7.58 (s, 2H); 7.39 (t, 2H); 3.60 (s, 2H); 0.61 (s, 9H).

Preparation 4A

Alternate Procedure

1-[2-Amino-3-(2,2-dimethylpropyl)imidazo[4,5-b]pyridin-5-yl]-2-(4-fluorophenyl)ethane-1,2-dione 3-(2,2-Dimethylpropyl)-5-[(E)-2-(4-fluorophenyl)vinyl]imidazo[4,5-b]pyridin-2-amine (1.00 g, 2.93 mmol) is suspended in 1,4-dioxane (4 mL) and 50% sulfuric acid (1 mL) in a 3-neck, round-bottomed flask equipped with a thermocouple and reflux condenser. The mixture becomes a clear solution and is heated to reflux (90-93° C. internal and 115° C. oil bath temperature). Hydrogen bromide (400 μL, 3.56 mmol) and dimethyl sulfoxide (2.50 mL, 35.20 mmol) are added respectively. The reaction mixture is heated at reflux using an oil bath and nitrogen was introduced at a rate of about one bubble/second. After 1 hour, a second portion of 50% sulfuric acid (3 mL, 21.4 mmol) is added. After 5 hours, a third portion of 50% sulfuric acid (4 mL, 31 mmol) is added and the reaction is continued under reflux overnight. HPLC analysis shows the product to be >93%. The oil bath is removed and the reaction allowed to cool to about 70° C. at which time water (5 mL) is added. After cooling to room temperature (about 30 minutes) the mixture is filtered, and the cake is washed with water (10 mL) to obtain the hydrogen sulfate salt of the product (1.33 g).

The above salt is added to 1 N sodium hydroxide (50 mL) and stirred at room temperature for 30 minutes to obtain a light yellow suspension. The mixture is filtered and the light yellow solid washed with water (3×10 mL) and then dried at 55° C. under vacuum to provide the title compound (0.91 g, 88%).

REFERENCE EXAMPLE 1

5-[2-tert-Butyl-5-(4-fluorophenyl)-1H-imidazol-4-yl]-3-(2,2-dimethylpropyl)imidazo[4,5-b]pyridin-2-amine dimethanesulfonate or 5-[2-tert-Butyl-5-(4-fluoro-phenyl)-1H-imidazol-4-yl]-3-(2,2-dimethyl-propyl)-3H-imidazo[4,5-b]pyridin-2-ylamine dimethansulfonate

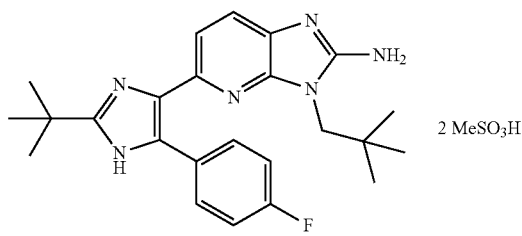 [SMILES: CC(C)(C)Cn1c(N)nc2ccc(-c3nc(C(C)(C)C)[nH]c3-c3ccc(F)cc3)nc21]

1-[2-Amino-3-(2,2-dimethylpropyl)imidazo[4,5-b]pyridin-5-yl]-2-(4-fluorophenyl)ethane-1,2-dione (354 g, 1 mol) is mixed with ethanol (2.8 L), ammonium acetate (550.0 g, 7.1 mol), and trimethyl acetaldehyde (110 g, 1.3 mol). The reaction is heated at about 70° C. (the reaction temperature is kept below refluxing to help suppress the sublimation of NH$_4$OAc) until the disappearance of the dione as monitored by HPLC or LC-MS. After the completion of the reaction (usually overnight), the mixture is concentrated under vacuum. Ethyl acetate (5.3 L) and water (3.5 L) are added, followed by 1 N NaOH (1.4 L). The mixture is stirred for 20-30 minutes at room temperature. The phases are separated and the aqueous phase is extracted with ethyl acetate (2.8 L). The combined ethyl acetate portions are washed twice with 10 volumes of brine. The ethyl acetate solution is evaporated to about 1.2 L (about 3 volumes). Ethanol (2.8 L) is added and the mixture heated to about 65° C. Methanesulfonic acid (240.0 g, 2.5 mol) in ethyl acetate (600 mL) is added in a fast dropwise fashion. The mixture is maintained at about 65° C. for 3 hours. The heat source is removed and the reaction is cooled to room temperature with stirring for 2 hours more. The solid product is collected by filtration, rinsed with ethyl acetate (500 mL), and dried in a vacuum oven at about 45° C. to obtain the title compound (490 g, 80%). ES/MS m/z 421.5 (M+1). $^1$H NMR (300 MHz, DMSO-d$_6$): δ 8.99 (s, 2H), 7.90 (d, 1H, J=9.0 Hz); 7.86 (d, 1H, J=9.0 Hz); 7.60 (dd, 2H, J=9.0 Hz), 7.34 (dd, 2H, J=9.0 Hz); 3.68 (s, 2H); 2.35 (s, 6H); 1.51 (s, 9H); 0.71 (s, 9H).

The following Examples illustrate improved efficacy of the triple combination administration of the compounds, 5-[2-tert-butyl-5-(4-fluoro-phenyl)-1H-imidazol-4-yl]-3-(2,2-dimethyl-propyl)-3H-imidazo[4,5-b]pyridin-2-ylamine (dimethanesulfonate salt (Compound A)), gemcitabine, and a platinum agent over the dual combination of gemcitabine and a platinum agent in mouse xenograft studies of human ovarian cancer. It should be understood that the Examples are set forth by way of illustration and not limitation, and that various modifications may be made by one of ordinary skill in the art.

EXAMPLE 1

In Vivo Triple Combination with Compound a, Gemcitabine, and Cisplatin

The purpose of this study is to compare the dual combination treatment of gemcitabine and cisplatin and the triple combination treatment (including Compound A) in a xenograft mouse model of human ovarian cancer to determine which is more efficacious.

Human tumor mouse xenografts are generated from early passages of the following ovarian cancer cell lines: A-2780 (National Cancer Institute), SK-OV-3x.luc (SK-OV-3 cell line modified to express luciferase (#1, medium expressing), Indiana University). A-2780 ovarian cancer cells are grown in RPMI 1640 with L-glutamine, 25 mM HEPES (Invitrogen 22400-089) supplemented with 1 mM pyruvate and 10% Certified Fetal Bovine Serum (Gibco 16000, FBS). SK-OV-3x.luc cells (ovarian cancer cells) are grown in McCoy's 5A Medium with L-glutamine (Invitrogen 16600-082) supplemented with non-essential amino acids, 1 mM pyruvate and 10% FBS.

Harlan athymic nude mice (6-7 weeks old) are housed with ad libitum feed and water, and are acclimated for one week prior to subcutaneous xenograft implantation in the right rear flank with a defined number of cells. A-2780 or SK-OV-3x.luc implants consist of 0.1 mL of cells (2 or 5×10$^6$ cells, respectively) in serum-free media with 0.1 mL MATRIGEL® (BD Biosciences) for a final volume of 0.2 mL. Tumors are allowed to develop to a volume of 120-150 mm$^3$ and are then randomized into treatment groups to attain a consistent average tumor size across all groups. Each treatment group of the SK-OV-3x.luc study is 12 animals; each group of the A-2780 study is 20 animals.

Compound A is prepared weekly in hydroxyethylcellulose (HEC) 1%/TWEEN® 80 0.25%/Antifoam 0.05% (HEC/TWEEN®) and stored at 4° C. A dose of 30 mg/kg Compound A for the SK-OV-3x.luc treatment group (or 10 mg/kg for the A-2780 treatment group), or its vehicle, is administered orally by gastric gavage three times daily (TID) in a volume of 0.2 mL for 3 weeks. The treatment protocol includes a two day initial treatment with Compound A prior to introduction of the gemcitabine and cisplatin treatments.

Cisplatin and gemcitabine are diluted in PBS, prepared and administered weekly as 0.2 mL intraperitoneal injections. The volume is administered as a constant as illustrated in Table 1.

TABLE 1

| Gemcitabine | |
| --- | --- |
| 100 mg/kg | 0.2 mL |
| 50 mg/kg | 0.2 mL |
| 25 mg/kg | 0.2 mL |
| Cisplatin at: | |
| 4 mg/kg | 0.2 mL |
| 2 mg/kg | 0.2 mL |
| 1 mg/kg | 0.2 mL |

Once weekly (QW) treatments of gemcitabine and cisplatin are given commencing on the third day at 0.5 and 1 hour, respectively, after the 7th dose (corresponding to just over two full days of Compound A dosing) of Compound A or vehicle each week. The highest doses of gemcitabine and cisplatin are selected based on efficacy as single agents, and fixed ratio dilutions of these are dosed in combination (sequential administration as separate compounds): 100 mg/kg gemcitabine+4 mg/kg cisplatin (100+4); 50 mg/kg gemcitabine+2 mg/kg cisplatin (50+2); or 25 mg/kg gemcitabine+1 mg/kg cisplatin (25+1). The SK-OV-3x.luc and A-2780 treatment groups are administered the triple combination therapy according to the following dosing regimens. Corresponding vehicles are employed where no treatment is indicated.

1. HEC/TWEEN®, 0.2 mL, oral, TID×21/PBS, 0.2 mL+0.2 mL, IP, QW×3
2. Compound A, 10 (or 30) mg/kg, oral, TID×21/PBS, 0.2+0.2 mL, IP, QW×3
3. HEC/TWEEN®, 0.2 mL, oral, TID×21/gemcitabine+cisplatin (25+1) mg/kg, IP, QW×3
4. HEC/TWEEN®, 0.2 mL, oral, TID×21/gemcitabine+cisplatin (50+2) mg/kg, IP, QW×3
5. HEC/TWEEN®, 0.2 mL, oral, TID×21/gemcitabine+cisplatin (100+4) mg/kg, IP, QW×3
6. Compound A, 10 (or 30) mg/kg, oral, TID×21/gemcitabine+cisplatin, 25+1 mg/kg, IP, QW×3
7. Compound A, 10 (or 30) mg/kg, oral, TID×21/gemcitabine+cisplatin, 50+2 mg/kg, IP, QW×3
8. Compound A, 30 mg/kg, oral, TID×21/gemcitabine+cisplatin, 100+4 mg/kg, IP, QW×3*

*SK-OV-3x.luc study only

Tumor volume and body weight are recorded and analyzed twice weekly using a data capture and analysis tool. Tumor volume (mm$^3$) is estimated by using the formula: $v=l \times w^2 \times 0.536$ where l=larger of measured diameter and w=smaller of perpendicular diameter. Antitumor activity is calculated as a percent reduction of treated (T) tumor volume relative to untreated control (C) tumor volume [1−(T/C)]×100. Tumor volume data are transformed to a log scale to equalize variance across time and treatment groups. The log volume data are analyzed with a two-way repeated measures analysis of variance by time and treatment using the MIXED procedures in SAS software (version 8.2). The correlation model for the repeated measures is spatial power. Treated groups are compared to the control group at each time point. The MIXED procedure is also used separately for each treatment group to calculate adjusted mean and standard error at each time point. Both analyses account for the autocorrelation within each animal and the loss of data that occurs when animals with large tumors are removed from the study early. The adjusted mean and standard error are plotted for each treatment group versus time. By convention, p-values ≤0.05 indicate significant differences in tumor growth. Maximal percentage of weight loss and final tumor volume measurements are presented with the resultant statistical comparison of tumor growth inhibition between the individual and combination treatments.

The final average tumor volume of SK-OV-3x.luc xenografts treated for 3 weeks with Compound A alone, or with lower dose combinations of gemcitabine and cisplatin (25+1, 50+2) administered on a once weekly schedule, is not significantly different from vehicle control (Table 2). The highest gemcitabine+cisplatin combination (100+4) yields tumor growth inhibition relative to vehicle control. The co-treatment of each of the gemcitabine+cisplatin treated animals with Compound A results in an enhancement of tumor growth inhibition. The combinations of 25+1, 50+2 and 100+4 with Compound A achieve or surpass the antitumor response to the 100+4 combination.

The triple combination treatment of each of the 25+1 and 50+2 gemcitabine+cisplatin treated animals with Compound A results in an improvement of tumor growth inhibition over the dual combination of gemcitabine+cisplatin as shown in Table 2. Specifically, the combinations of 25+1, 50+2, and 100+4 with Compound A significantly surpass the antitumor response to their respective 25+1, 50+2, and 100+4 dual combination.

TABLE 2

SK-OV-3x.luc tumor growth inhibition with gemcitabine, cisplatin and Compound A combination treatments

| | Max % wt. loss | final tumor volume | significance (p values) | | | final n |
| --- | --- | --- | --- | --- | --- | --- |
| | | | vehicle | A | (G + C)[1] | |
| vehicle | 0.0 | 505 ± 51 | — | — | — | 12 |
| A | 1.4 | 522 ± 54 | NS | — | — | 10 |
| 25 + 1 | 5.2 | 407 ± 39 | NS | NS | — | 12 |
| 50 + 2 | 4.1 | 524 ± 54 | NS | NS | — | 12 |
| 100 + 4 | 13.7 | 337 ± 43 | 0.010 | 0.007 | — | 11 |
| 25 + 1/A | 5.4 | 253 ± 42 | <0.001 | <0.001 | 0.002 | 11 |
| 50 + 2/A | 7.7 | 364 ± 30 | 0.030 | 0.021 | 0.017 | 10 |
| 100 + 4/A | 13.1 | 202 ± 15 | <0.001 | <0.001 | 0.001 | 11 |

[1]Each gemcitabine + cisplatin (G + C)/A combination is compared to its matched combination (G + C) only.

In a second model, A2780 ovarian tumor model, the triple combination treatment of each of the gemcitabine+cisplatin treated animals with Compound A results in an improvement of tumor growth inhibition over the dual combination of gemcitabine+cisplatin, as shown in Table 3. Specifically, the combinations of 25+1 and 50+2 with Compound A significantly surpass the anti-tumor response to the 25+1 and 50+2 dual combination.

TABLE 3

A-2780 tumor growth inhibition with gemcitabine, cisplatin and Compound A combination treatments

| | Max % wt. loss | final tumor volume | significance (p values) | | | final n |
| --- | --- | --- | --- | --- | --- | --- |
| | | | vehicle | A | (G + C)[1] | |
| vehicle | 1.8 | 2257 ± 279 | — | — | — | 20 |
| A | 3.0 | 1828 ± 208 | NS | — | — | 20 |
| 25 + 1 | 4.6 | 536 ± 58 | <0.001 | <0.001 | — | 19 |
| 50 + 2 | 5.1 | 381 ± 39 | <0.001 | <0.001 | — | 19 |
| 100 + 4 | 7.4 | 219 ± 22 | <0.001 | <0.001 | — | 20 |
| 25 + 1/A | 7.9 | 361 ± 34 | <0.001 | <0.001 | 0.009 | 19 |
| 50 + 2/A | 8.6 | 218 ± 14 | <0.001 | <0.001 | <0.001 | 20 |

[1]Each gemcitabine + cisplatin (G + C)/A combination is compared to its matched combination (G + C) only. (100 + 4) is not evaluated in combination with Compound A.

EXAMPLE 2

In vivo Triple Combination Therapy with Compound A, Gemcitabine, and Carboplatin Carboplatin (25 mg/kg-100 mg/kg) may be substituted for cisplatin essentially as described in Example 1.

The compounds described in the present invention are preferably formulated as pharmaceutical compositions administered by a variety of routes. Most preferably, such compositions are for oral, intravenous, or intraperitoneal administration. Such pharmaceutical compositions and processes for preparing the same are well known in the art. See, e.g., REMINGTON: THE SCIENCE AND PRACTICE OF PHARMACY (D. Troy, et al., eds., 21$^{st}$ ed., Lippincott Williams & Wilkins, 2005).

The compounds of the present invention are generally effective over a wide dosage range. The amount of 5-[2-tert-butyl-5-(4-fluoro-phenyl)-1H-imidazol-4-yl]-3-(2,2-dimethyl-propyl)-3H-imidazo[4,5-b]pyridin-2-ylamine administered normally falls within the range of about 100-420 mg every 12 hours for 10 days, more preferably 100-300 mg every 12 hours for 10 days, and most preferably 200 mg every 12 hours for 10 days or alternatively 300 mg every 12 hours for 10 days. It is anticipated that 5-[2-tert-butyl-5-(4-fluoro-phenyl)-1H-imidazol-4-yl]-3-(2,2-dimethyl- propyl)-3H-imidazo[4,5-b]pyridin-2-ylamine will be administered for at least two days prior to the initiation of the gemcitabine and cisplatin or gemcitabine and carboplatin regimen.

According to the FDA approved dosing regimen, the combination administration of gemcitabine and carboplatin should be administered intravenously at a dose of 1000 mg/m2 over 30 minutes on days 1 and 8 of each 21-day treatment cycle. Carboplatin AUC 4 should be administered intravenously on day 1 after gemcitabine administration. Patients should be monitored prior to each dose with a complete blood count, including differential counts. Patients should have an absolute granulocyte count >1500×106/L and a platelet count >100,000×106/L prior to each cycle.

Dose Modifications

Gemcitabine dosage adjustment for hematological toxicity within a cycle of treatment is based on the granulocyte and platelet counts taken on day 8 of therapy. If marrow suppression is detected, gemcitabine dosage should be modified according to guidelines in Table 4.

TABLE 4

Day 8 Dosage Reduction Guidelines for Gemcitabine in Combination with Carboplatin

| Absolute granulocyte count (×10$_6$/L) | | Platelet count (×10$_6$/L) | % of full dose |
|---|---|---|---|
| ≥1500 | and | ≥100,000 | 100 |
| 1000-1499 | and/or | 75,000-99,999 | 50 |
| <1000 | and/or | <75,000 | Hold |

In general, for severe (Grade 3 or 4) non-hematological toxicity, except nausea/vomiting, therapy with gemcitabine should be held or decreased by 50% depending on the judgment of the treating physician. For carboplatin dosage adjustment, see manufacturer's prescribing information.

Dose adjustment for gemcitabine in combination with carboplatin for subsequent cycles is based upon observed toxicity. The dose of gemcitabine in subsequent cycles should be reduced to 800 mg/m$^2$ on days 1 and 8 in case of any of the following hematologic toxicities:

Absolute granulocyte count <500×10$^6$/L for more than 5 days

Absolute granulocyte count <100×10$^6$/L for more than 3 days febrile neutropenia Platelets <25,000×10$^6$/L Cycle delay of more than one week due to toxicity If any of the above toxicities recur after the initial dose reduction, for the subsequent cycle, gemcitabine should be given on day 1 only at 800 mg/m$^2$.

It is believed that cisplatin could be administered in a similar manner to carboplatin.

In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A method of treating ovarian cancer in a mammal comprising administering to said mammal a combination of gemcitabine, a platinum agent selected from the group consisting of cisplatin and carboplatin, and 5-[2-tert-butyl-5-(4-fluoro-phenyl)-1H-imidazol-4-yl]-3-(2,2-dimethyl-propyl)-3H-imidazo[4,5-b]pyridin-2-ylamine or a pharmaceutically acceptable salt thereof.

2. The method of claim 1 wherein gemcitabine and the platinum agent are administered up to 2 days after 5-[2-tert-butyl-5-(4-fluoro-phenyl)-1H-imidazol-4-yl]-3(2,2-dimethyl-propyl)-3H-imidazo[4,5-b]pyridin-2-ylamine or a pharmaceutically acceptable salt thereof is administered and gemcitabine is administered again up to 7 days later.

3. The method according to claim 1 wherein the administration is during a 21-day treatment cycle.

4. The method according to claim 1 wherein the pharmaceutically acceptable salt is dimethanesulfonate salt.

5. The method according to claim 2 wherein the administration is during a 21-day treatment cycle.

6. The method according to claim 2 wherein the pharmaceutically acceptable salt is dimethanesulfonate salt.

7. The method according to claim 2 wherein the 5-[2-tert-butyl-5-(4-fluoro-phenyl)-1H -imidazol-4-yl]-3-(2,2-dimethylpropyl)-3H-imidazo[4,5-b]pyridine-2-ylamine or the salt thereof is administered at 200 mg or 300 mg.

8. The method according to claim 7 wherein gemcitabine is administered at 1000 mg/m$^2$ intravenously over 30 minutes on days 3 and 10 and the platinum agent is carboplatin AUC 4 and is administered intravenously over 30 minutes on day 3.

9. The method according to claim 2 wherein the 5-[2-tert-butyl-5-(4-fluoro-phenyl)-1H -imidazol-4-yl]-3-(2,2-dimethylpropyl)-3H-imidazo[4,5-b]pyridine-2-ylamine or the salt thereof is administered at 200 mg every 12 hours on days 1-10 of a 21-day treatment cycle.

10. The method according to claim 9 wherein gemcitabine is administered at 100 mg/m$^2$ intravenously over 30 minutes on days 3 and 10 and the platinum agent is carboplatin AUC 4 and is administered intravenously over 30 minutes on day 3.

* * * * *

UNITED STATES PATENT AND TRADEMARK OFFICE
CERTIFICATE OF CORRECTION

PATENT NO. : 9,844,529 B2
APPLICATION NO. : 14/354244
DATED : December 19, 2017
INVENTOR(S) : Edward Michael Chan, Susan Elizabeth Pratt and Louis Frank Stancato It is certified that error appears in the above-identified patent and that said Letters Patent is hereby corrected as shown below:

On the Title Page

Column 2, Other Publications, Line 3, please delete "antiinflanmatory" and insert --anti inflammatory--, therefor.

In the Claims

In Column 12, Line 36, in Claim 2, please delete "pyridin-2" and insert --pyridine-2--, therefor.

In Column 12, Line 48, in Claim 7, please delete "1H -imidazol" and insert --1H-imidazol--, therefor.

In Column 12, Line 57, in Claim 9, please delete "1H -imidazol" and insert --1H-imidazol--, therefor.

In Column 12, Line 62, in Claim 10, please delete "100" and insert --1000--, therefor.

Signed and Sealed this
Thirteenth Day of March, 2018

Andrei Iancu
*Director of the United States Patent and Trademark Office*